(12) United States Patent
Szymaitis (10) Patent No.: US 10,004,806 B2
(45) Date of Patent: *Jun. 26, 2018

(54) PERIODONTAL REGENERATION COMPOSITION AND METHOD OF USING SAME

(71) Applicant: Dennis W. Szymaitis, Pittsburgh, PA (US)

(72) Inventor: Dennis W. Szymaitis, Pittsburgh, PA (US)

(73) Assignee: Periovance, Inc., Pittsburgh, PA (US)

( * ) Notice: Subject to any disclaimer, the term of this patent is extended or adjusted under 35 U.S.C. 154(b) by 672 days.

This patent is subject to a terminal disclaimer.

(21) Appl. No.: 13/655,969

(22) Filed: Oct. 19, 2012

(65) Prior Publication Data

US 2013/0101641 A1   Apr. 25, 2013

Related U.S. Application Data (60) Continuation of application No. 11/511,052, filed on Aug. 28, 2006, now Pat. No. 8,313,328, which is a division of application No. 10/406,395, filed on Apr. 3, 2003, now Pat. No. 7,105,182, which is a continuation-in-part of application No. 09/912,930, filed on Jul. 25, 2001, now abandoned.

(51) Int. Cl.
| | |
|---|---|
| *A61K 45/06* | (2006.01) |
| *A61K 33/42* | (2006.01) |
| *A61K 33/06* | (2006.01) |
| *A61K 38/39* | (2006.01) |
| *A61L 27/24* | (2006.01) |
| *A61L 27/26* | (2006.01) |
| *A61L 27/36* | (2006.01) |
| *A61L 27/44* | (2006.01) |
| *A61L 27/46* | (2006.01) |
| *A61L 27/50* | (2006.01) |
| *A61L 27/52* | (2006.01) |
| *A61L 27/54* | (2006.01) |

(52) U.S. Cl.
CPC ............. *A61K 45/06* (2013.01); *A61K 33/06* (2013.01); *A61K 33/42* (2013.01); *A61K 38/39* (2013.01); *A61L 27/24* (2013.01); *A61L 27/26* (2013.01); *A61L 27/3608* (2013.01); *A61L 27/3641* (2013.01); *A61L 27/446* (2013.01); *A61L 27/46* (2013.01); *A61L 27/50* (2013.01); *A61L 27/502* (2013.01); *A61L 27/52* (2013.01); *A61L 27/54* (2013.01); *A61L 2300/404* (2013.01); *A61L 2300/41* (2013.01); *A61L 2300/414* (2013.01); *A61L 2400/06* (2013.01); *A61L 2430/12* (2013.01); *Y10S 435/808* (2013.01)

(58) Field of Classification Search
USPC ........................................ 523/115; 525/54.1
See application file for complete search history.

(56) References Cited

U.S. PATENT DOCUMENTS

| | | | |
|---|---|---|---|
| 4,321,038 A | 3/1982 | Porteous | |
| 4,394,370 A | 7/1983 | Jefferies | |
| 4,472,840 A | 9/1984 | Jefferies | |
| 4,685,883 A | 8/1987 | Jernberg | |
| 4,774,227 A | 9/1988 | Piez et al. | |
| 4,789,663 A | 12/1988 | Wallace et al. | |
| 4,795,467 A | 1/1989 | Piez et al. | |
| 4,938,763 A | 7/1990 | Dunn et al. | |
| 5,073,114 A | 12/1991 | Detsch | |
| 5,077,049 A | 12/1991 | Dunn et al. | |
| 5,123,925 A | 6/1992 | Smestad et al. | |
| 5,171,148 A | 12/1992 | Wasserman et al. | |
| 5,197,882 A | 3/1993 | Jernberg | |
| 5,292,253 A | 3/1994 | Levy | |
| 5,324,519 A | 6/1994 | Dunn et al. | |
| 5,330,357 A | 7/1994 | Keller | |
| 5,352,715 A | 10/1994 | Wallace et al. | |
| 5,362,495 A | 11/1994 | Lesage | |
| 5,366,507 A | 11/1994 | Sottosanti | |
| 5,422,340 A | 6/1995 | Ammann | |
| 5,433,751 A | 7/1995 | Christel et al. | |
| 5,462,722 A | 10/1995 | Liu et al. | |
| 5,550,188 A | 8/1996 | Rhee et al. | |
| 5,569,308 A | 10/1996 | Sottosanti | |
| 5,607,689 A | 3/1997 | Checchi | |

(Continued)

FOREIGN PATENT DOCUMENTS

| WO | 98/40113 | 9/1998 |
|---|---|---|
| WO | 00/15274 | 3/2000 |

OTHER PUBLICATIONS

"New Treatment for Osseous Defects Available", JADA, vol. 130, Dec. 1999, p. 1698.
"Bone Grafting Materials for Dental Applications: A Practical Guide", Compendium, Oct. 1997, pp. 1013-1016, 1020-1022, 1024, 1026, 1030, 1032, 1034 1-36.
Courtney, Fundamentals of Structural Adhesives for Device Assembly, Medical Device & Diagnostic Industry, Jul. 1997, pp. 105-110.
BioCore Medical Technologies, Inc. Product Information with Kollagen Technology Brochure, Mar. 24, 1999, pp. 1-19.

*Primary Examiner* — Walter E Webb
(74) *Attorney, Agent, or Firm* — Pepper Hamilton LLP (57) ABSTRACT

A periodontal structure regeneration composition for treatment of periodontal disease is a mixture of particles of a bone growth material and free collagen. All particles are sized to be less than 1 mm in diameter. The periodontal regeneration composition is injected into the periodontal pocket through an 18 gauge needle. The composition may contain a thickener that increases the viscosity of the composition after the material has been injected into the periodontal pocket. The composition is available in pre-filled syringes offered in a kit that may also contain strips of surgical sponge or gauze that are sized to fit within a periodontal pocket, a time of adhesive, a dental bur, a probe, a gauze placement tool, gauze counter and a brush for cleaning the dental bur.

21 Claims, 3 Drawing Sheets

(56) References Cited

U.S. PATENT DOCUMENTS

| | | |
|---|---|---|
| 5,620,700 A | 4/1997 | Berggren et al. |
| 5,676,976 A | 10/1997 | Lee et al. |
| 5,683,461 A | 11/1997 | Lee et al. |
| 5,702,716 A | 12/1997 | Dunn et al. |
| 5,707,962 A | 1/1998 | Chen et al. |
| 5,866,165 A | 2/1999 | Liu et al. |
| 6,180,606 B1 | 1/2001 | Chen et al. |
| 6,352,704 B1 | 3/2002 | Nicholson et al. |

PERIODONTAL REGENERATION COMPOSITION AND METHOD OF USING SAME

CROSS REFERENCE TO RELATED APPLICATIONS

This is a continuation of U.S. patent application Ser. No. 11/511,052, filed Aug. 28, 2006, now U.S. Pat. No. 8,313,328 which was a divisional of U.S. patent application Ser. No. 10/406,395, now U.S. Pat. No. 7,105,182, which was a continuation in part of U.S. patent application Ser. No. 09/912,930, filed Jul. 25, 2001, now abandoned.

FIELD OF INVENTION

The invention relates to a bone growth and periodontal structure regeneration material, and method for treating periodontal disease.

BACKGROUND OF THE INVENTION

Periodontal disease occurs when bacteria colonize the sulcus space between the teeth and gingiva. The bacteria cause inflammation. The inflammation destroys the gingival epithelial lining and epithelial attachment to the tooth. The inflammation then progresses down the tooth root toward the apex of the root and destroys periodontal structure and bone. As periodontal disease progresses open pockets develop between the tooth and the gingiva. A dentist can determine the presence and extent of periodontal disease using a probe to measure the depth of pockets between each tooth and gingiva. X-rays can reveal the extent of any bone loss.

A common surgical procedure has been widely used to treat bone loss caused by periodontal disease. In this procedure the periodontist uses a scalpel to incise the gingiva and reflects it back to expose the tooth root and bone. Then he removes the irregular shaped bone with hand instruments or rotary instruments, surgically removes granulation tissue and gingiva, cleans the site and places a bone regeneration material into osseous detects that remain in the bone. Guided Tissue Regeneration barriers are placed over bone regeneration material in deeper osseous defects. He then sutures the gingiva around the tooth. Then the gingiva, epithelial attachment, bone, and periodontal ligament between the tooth and bone reform. While this procedure has been effective, incisions in the gingiva cause patient discomfort, pain, swelling, gingival recession, sensitive teeth, a long healing time, and increase the possibility of infection. The goal of visualization of the roots, removal of granulation tissue, and excision of damaged gingiva utilizing traditional incision periodontal surgery on a normal compliment of 28 teeth requires a cumulative incision length of 41 to 46 inches. The extensive cumulative length of surgical incisions wears down the scalpel cutting edge. It is common surgical practice to use and discard between 4 to 10 Bard Parker #15 surgical scalpel blades for each patient. To reposition all of the surgically loosened gingiva requires between 4 to 8 suture packets of 18 inch suture. The volume of granulation tissue and gingiva removed is approximately 2 to 5 cc. Estimated blood loss varies 2 cc to 18 cc per patient. The post-surgical period requires strong analgesics to maintain pain relief. At the 2 week suture removal appointment, the gingival incisions are only about 50% healed, and require 2 to 4 additional weeks for final healing. The period of painful, sensitive, and bleeding gingiva lasts 3 to 4 weeks after the surgery. After this struggle to gain periodontal health, the patient now faces gingival recession with exposed sensitive roots resulting from granulation and gingiva removal. Cosmetic difficulties result from the loss of the interdental gingiva that creates dark spaces between the teeth. The exposure of the margins of facings and crowns often requires replacement to correct cosmetic deficiencies.

Consequently, there is also a need for a procedure for reversing bone loss and periodontal structure damage caused by periodontal disease. There is also a need for a regeneration material that could be used without incisions to regenerate bone and periodontal structure lost to periodontal disease. Periodontal therapy without incisions, eliminates discomfort pain, swelling, gingival recession, sensitive teeth, greatly shortens healing time, and greatly decreases potential for infections.

A variety of materials are available and have been used for bone regeneration. Autogenous bone has long been considered the "gold standard" of bone grafting material. This is bone material taken from other parts of a patient's body. The primary shortcomings in the use of autogenous bone is the need for a second operative site, the attendant patient morbidity and the possibility of being unable to obtain sufficient material. The art has also used bone particles taken from cadavers. These bone particles may be frozen, freeze-dried, demineralized freeze-dried and irradiated. Patients are reluctant to accept cadaver bone because health of the recipient may depend upon the health history of the donor. Consequently, other bone growth materials, not taken from humans, are more frequently used for bone regeneration.

Over the last two decades, ceramics, such as hydroxylapatite and tricalcium phosphate, and polymers have received the most attention as substitutes for autogenous bone grafts. Calcium phosphate ceramics act through osteoconduction by providing a scaffold for enhanced bone tissue repair and growth.

Calcium carbonate is another inorganic material used for bone grafting. It has been reported that a natural coral containing over 98% calcium carbonate and sold under the trademark BioCoral is effective as a bone growth material for periodontal disease. This material is provided as granules 300 microns to 400 microns in diameter.

Another bone graft material is a synthetic bone sold under the trademark Bioplant HJR. This material contains a calcium hydroxide in a co-polymer of polyhydroxyehyl methacrylate and polymethyl-methacrylate. This material is also provided and used in granular form.

It is well known to combine other materials with bone growth materials when used to promote bone growth. Calcium sulfate hemihydrate, also known as medical grade plaster, is often combined with hydroxylapatite to provide initial stabilization and prevent migration to surrounding soft tissues. The calcium sulfate is resorbed by the body within one month leaving a scaffold of hydroxylapatite for bone growth. Chen et al. in U.S. Pat. No. 5,707,962 teach that growth factors, such as collagen, nutrient factors, drugs, anti-microbial agents, calcium containing compounds, blood proteins or products and anti-inflammatory agents may be combined with the matrix or scaffold forming material such as hydroxylapatite. The patent teaches that deminerialized bone particles or powder or Bone Morphogenic Protein or proteins be added to collagen powder or fleece to form a bone sponge. The parent teaches that chips of this sponge or sponge ground into powder or fleece can be used. Collagen in this form is not free to react with body tissue like collagen powder. Chen et al. do not teach how the compositions they disclosed are to be used except for saying they are implanted by standard surgical or dental procedures.

U.S. Pat. No. 5,292,253 describes a procedure in which missing bone is filled with a mass of calcium phosphate or hydroxylapatite and covered with a gel containing a collagen, fibrin or gelatin and a dye. The gel is then exposed to laser radiation to weld the calcium containing material to the bone. This is an expensive treatment and puts the patient at risk of exposure to harmful laser radiation, particularly if the patient moves an eye into the path of the laser.

U.S. Pat. No. 5,352,715 discloses an injectable composition of collagen and mineral materials, such as hydroxyapatite or tricalcium phosphate. The composition also includes a carrier such as polyethylene glycol, hyaluronic acid and poly(hydroxyethyl methactylate) which makes the composition a gel. The gel is injected through a needle. The composition may also include lubricants, such as glycerin, which allow the composition to pass more easily through a needle. That needle has a diameter of 20 gauge or smaller. The organic polymers and any collagen in the composition do not act as a matrix but are absorbed by the body, leaving the ceramic material as the supporting matrix. Although the patent says that the material is an injectable implant composition that can be used for bone repairs, there is no teaching that the material can be used to treat periodontal disease. The patent teaches that any type of collagen can be used. There is also no teaching that the composition change viscosity or harden shortly after injection.

All present periodontal surgery methods require incisions to allow removal of bone, soft tissue, and to allow visual inspection of the root surface. One problem associated with the use of the bone growth materials described above is that the particle sizes require incisions in the gingiva to apply the material. However, in addition to the problems mentioned above, surgical procedures always require more healing time than procedures that do not require incisions. However, the art has not developed a procedure for treating bone loss from periodontal disease that does not require incisions in the gingiva. Consequently, there is a need for a bone growth material that can be placed adjacent to a degenerated alveolar bone to promote bone growth without requiring incisions in the gingiva. There is also a need for a procedure to place such a material to reverse periodontal disease without incisions in a patient's gingiva. Such a procedure and material should not merely grow bone. Rather, they should result in reforming of the epithelial attachment and encourage periodontal structure regeneration.

Any composition that is injected into the periodontal pocket must not migrate out of the pocket after injection. While the injectable gel-type bone growth compositions disclosed in the prior art could be injected into the periodontal pocket, they would migrate out of the pocket before they would have much effect as a result of normal rebound or retraction of the distended pocket and movement of the mouth.

SUMMARY OF THE INVENTION

I provide a periodontal structure regeneration composition for treatment of periodontal disease that is a mixture of particles of a bone growth material and free collagen particles. Free collagen particles are not cross-linked and are available to speed healing. All particles are sized to be less than 1 mm in diameter to enable the composition to be injected into a periodontal pocket through an 18 gauge needle. A preferred embodiment of the composition contains a thickener that changes the viscosity of the composition after placement in a periodontal pocket. The change in viscosity makes the composition less likely to migrate out of the pocket. Alternatively, I place an adhesive over the tooth and the gingival after the composition has been injected to seal the pocket and prevent escape of the composition. The mixture may also contain at least one growth factor, nutrient factor, drug, calcium containing compound, anti-inflammatory agent, anti-microbial agent, antibiotic or a combination thereof.

The inner lining of the periodontal pocket and the outer surface of the root are removed by utilizing a specially designed dental bur. Without incisions, the dental bur is placed into the pocket and with appropriate motions, removes the inner lining of the pocket and removes the outer surface of the root. This process establishes a 1-1.5 mm space between the root and the gingival tissue. One or more uniquely shaped sponges are placed into a periodontal pocket to distend the pocket, create hemostasis, and decrease bacteria. The sponge is removed and the periodontal structure regeneration composition is then injected into the periodontal pocket through a needle and syringe. Optionally, an adhesive may be applied to seal the pocket.

I prefer to provide a kit containing one or more syringes each having a needle with a diameter not larger than 18 gauge and pre-filled with the periodontal regeneration composition. The kit also contains strips of surgical sponge or gauze that are sized to fit within a periodontal pocket. The kit may also contain a container of adhesive, dental burs, a probe, a gauze placement tool and a brush for cleaning the dental bur.

DESCRIPTION OF THE PREFERRED EMBODIMENTS

Figure 1:
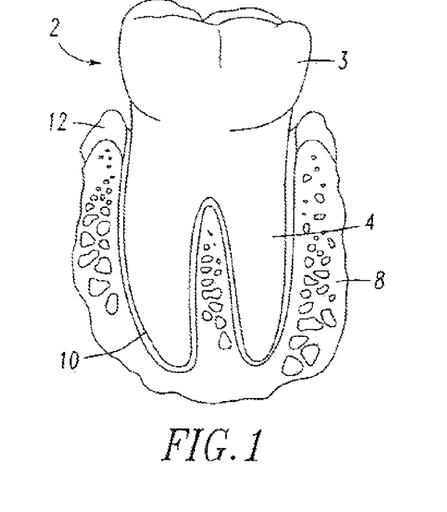
FIG. 1 is a front view of a healthy tooth.
Figure 2:
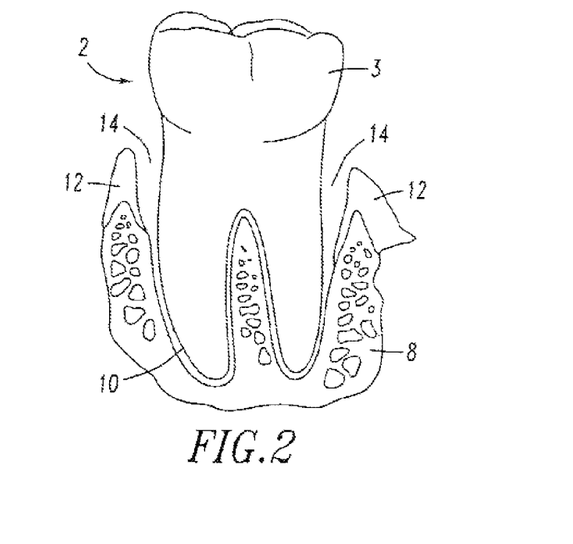
FIG. 2 is a front view of a tooth in a patient experiencing periodontal disease.
Figure 3:
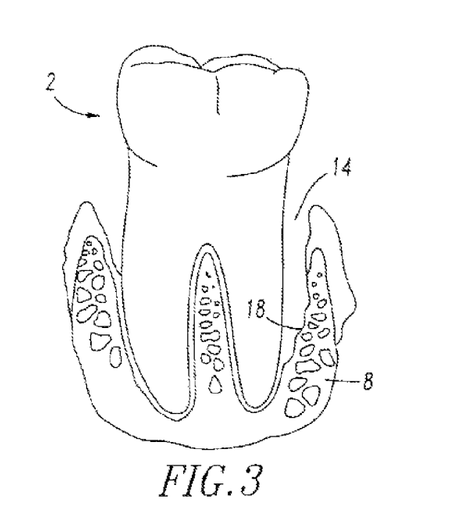
FIG. 3 is a front view of a tooth in a patient having advanced periodontal disease and bone loss.

As can be seen in FIG. 1 a tooth 2 has a crown 3 and root 4. The alveolar bone 8 surrounds the root 4. There is a periodontal ligament 10 around much of the root 4 and gingiva 12 surrounds the upper part of the root and the base of the crown 3. There is a pocket 14 between the gingiva 12 and the tooth 2. In a healthy tooth shown in FIG. 1 this pocket 14 is very shallow, typically one to three millimeters. Bacteria colonize the pocket. The bacteria cause the pocket 14 to deepen as shown in FIG. 2. As periodontal disease progresses the bacteria cause inflammation that destroys the ligament and bone creating depressions 18 in the bone shown in FIG. 3.

Figure 4:
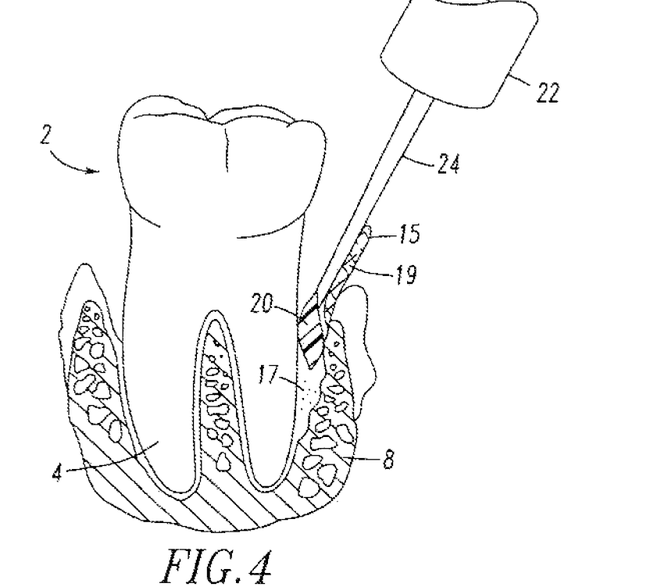
FIG. 4 is a front view of the diseased tooth of FIG. 3 being treated in accordance with the present invention.
Figure 5:
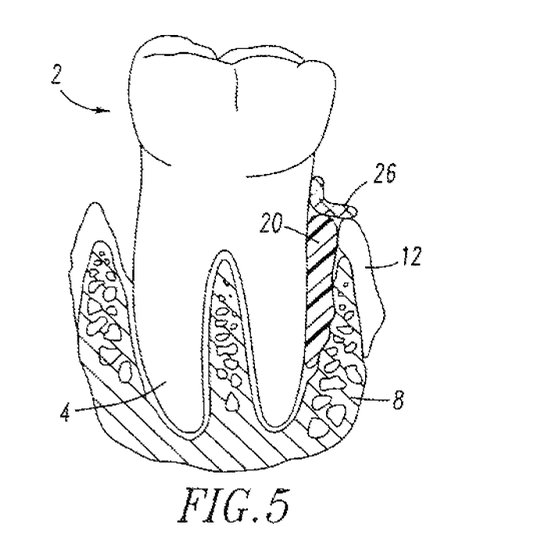
FIG. 5 is a front view of the diseased tooth of FIG. 3 immediately after completion of a treatment in accordance with one embodiment of the present invention.

The conventional way of treating advanced periodontal disease is to create incisions to reflect the gingiva 12, remove the damaged bone with hand instruments or sand area 18 with rotary burs, remove all debris from the sanding, place a bone growth material adjacent the sanded bone surfaces and suture the gingiva. The standard procedure for deeper osseous defects is to place expensive, and very difficult to manipulate, Guided Tissue Regeneration barriers over the bone regeneration material prior to suturing. I provide a method and material that does not involve incisions in the gingiva. Instead a bone growth material finely ground and mixed with fine collagen particles is injected into the pocket through a syringe. I abrade the root surface and inner surface of the gingiva first with a dental bur. I observed improved bone and periodontal structure regeneration if I did not rinse the abraded particles out of the pocket. Tooth dentin is a natural source of bone morphogenic protein and I utilize this source to promote bone generation. This failure to rinse is contrary to present dental practice. Standard periodontal practice is to completely clean the pocket of all abraded bone and to remove all granulation tissue. To abrade the root and gingival surfaces I simply place the dental bur into the pocket, but do not incise the gums. After abrading, specially designed gauze is placed into the 1-1.5 mm created space to both distend the pocket and create hemostasis with or without chemicals. I prefer to provide three sizes of gauze strips of 5 mm, 7.5 mm and 10 mm wide and 10 cm in length. As an additional use, the gauze can carry and place antibacterial materials, antibiotics, collagen, bone growth substances, or any type of root conditioning materials. Sufficient time is allowed for hemostasis, distention, and the placed materials to function as designed, then the gauze 15 is removed. As shown in FIG. 4, after abrading I inject a periodontal structural regeneration composition 20 into the pocket 14 through a syringe 22 and needle 24. This composition contains fine particles of bone growth material and free collagen particles all sized to be less than 1 mm in diameter. Free collagen particles are not cross-linked and are available to speed healing. The collagen may be small fibrils or a gel containing fibrillar collagen. A small amount of sterile saline or other liquid may be added. I prefer to use an 18 gauge needle because larger needles do not permit access to the small pockets found around the smaller anterior teeth. A 16 gauge needle could be used for treating molars suffering periodontal disease. Because an 18 gauge needle is needed to treat the anterior teeth, the particles in the periodontal structure regeneration composition 20 must be small enough to pass through an 18 gauge needle without clogging. Because the particles are so small the periodontal structure regeneration composition 20 looks like a gel as it exits the needle. This composition mixes with abraded root particles 17 in the pocket. Sufficient periodontal structure regeneration composition 20 is injected to fill the pocket as shown in FIGS. 4 and 5. The gingiva 12 then rebounds from the distension and moves back toward the tooth. Because the composition is injected into the periodontal pocket through a needle the viscosity has to be sufficient to pass through the needle but viscous enough to remain in the pocket. Some composition is forced from the pocket when the gingiva rebounds or returns to its normal position. But, most of the periodontal structure regeneration composition remains in the pocket. However, the viscosity of the composition that allows easy passage through the needle enables further migration from the periodontal pocket during normal movement of the mouth. To prevent that migration, it is preferred that a thickener be added to the composition, or that the composition be subjected to a brief infusion of energy, preferably but not exclusively by microwave radiation. A microwave exposure at power setting high for 20-40 seconds can be used. The composition will thicken a few minutes after being microwaved, allowing time for injection before the viscosity increases. The thickener or infusion of energy increases the viscosity of the composition after the composition has been injected into the periodontal pocket. The increase in viscosity is sufficient to prevent or retard migration or leakage of the composition from the pocket after the gingiva has rebounded to a relaxed position. Yet, the thickener does not cause the composition to form a rigid solid. The thickener also should not be a material that reacts with the collagen or causes the collagen in the composition to crosslink. The thickener must also be a physiologically compatible compound which does not injure or cause adverse reactions by the human body. This compound could be a liquid above normal body temperature and solidify at or below normal body temperature. The solidification of the thickener will increase the viscosity of the composition that is in the periodontal pocket but not cause the entire composition to become solid. This type of thickener could be an oligosaccharide such as certain polyethylene glycol compositions, that function this way. Another thickener that could be used is a chemical compound that slowly forms slightly soluble salts with one or more components of the composition, thus thickening the composition by giving it a larger percentage of solids after injection into the pocket. One could also put an adhesive in the composition that hardens in the presence of a catalyst, heat or light. There are polyurethanes which will set and then degrade over time. Certain silicones could also be used. Another method of thickening is formulating a composition that undergoes a phase change near physiological temperature to provide thickening. If this composition forms a eutectic mixture (solid and liquid (solution) phases existing in equilibrium) near physiological temperature, the cooling of a heated composition in the periodontal pocket would aid in prevention of the composition from migrating out of the periodontal pocket. Yet, another possibility is to use a hydrogel, corn starch or similar material that absorbs water and thereby thickens the composition. It is possible that this type of additive could draw water from tissue surrounding the periodontal pocket. For that reason only small amounts of this additive should be used, and the procedure may include putting water into the periodontal pocket immediately before injecting the composition. Those skilled in the art should recognize that other materials activated by air, heat, light or a catalyst could also be used as a thickener. Over time the periodontal regeneration composition causes both gingival growth, bone growth, and formation of a new epithelial attachment. Depending upon the extent of the disease, the teeth and bone will return to their healthy status shown in FIG. 1 in about 3 to 12 weeks.

In an alternative embodiment a thickener is not provided in the composition. When that composition is used, I prefer to apply an adhesive 26 over the pocket to eliminate any pain or discomfort, to stop any bleeding, to keep the regeneration material in place, and to prevent foreign material from entering the pocket and dislodging the regeneration material. However, I have found that bone regeneration and healing occurs even when no adhesive is used. I prefer to use butyl cyanoacrylate as the adhesive because this material cures with water. Another suitable water curable adhesive is 2-Octyl Cynoacrylate sold by Johnson & Johnson under the trademark DERMABOND. One could also use an adhesive that cures when exposed to light. Dentistry now uses polymers for filling cavities that cure when exposed to blue light. There are also adhesives that cure when exposed to ultraviolet light that could be used. However, far too many eye injuries caused by ultraviolet light have resulted in a general reluctance to use ultraviolet light in dentistry. There are adhesives that cure upon exposure to visible light which should be useful in this procedure. Other water curable adhesives, auto-curing adhesives, heat cured adhesives and reactive-component cure adhesives may also be acceptable.

I prefer to use hydroxylapatite as the bone growth material. Since I have not been able to find hydroxylapatite available in particle sizes small enough to pass through an 18 gauge needle without clogging, I have used 300 to 400 micron size hydroxylapatite particles and ground the material with a mortar and pestle. A very important advantage of using microcrystalline hydroxylapatite is that microcrystaline hydroxylapatite has been shown to have a much greater bone growth potential than the larger crystals of hydroxylapatite. One could also use calcium sulfate or a mixture of finely ground and larger particles of hydroxylapatite about, but not limited to, 50-400 micron and calcium sulfate as the bone growth material. There are other bone growth materials. One could use any other finely ground bone growth material, including human bone. Dunn et al. in U.S. Pat. No. 5,324,519 disclose a biodegradable polymer composition that can be used as a matrix to carry a variety of materials and act as an implant in animals. This composition is a thermoplastic or thermosetting polymer. One example given in the patent is a liquid mixture containing bone chips, bone morphogenetic protein and N-methyl pyrrolidone with PVP and DL-PLA polymers. Because of the bone chips this mixture would not be suitable for injection through an 18 gauge needle. However, if fine bone particles or fine particles of hydroxylapatite were substituted for the bone chips, this composition could be mixed with the collagen and used as the periodontal regeneration compound. Another suitable bone growth material is a synthetic peptide bound irreversibly to an inorganic bovine derived material and sold under the trademark PepGen P-15 by CeraMed Dental.

The periodontal structure regeneration material may also contain a root treatment material such as a bone morphogenic protein or a dental matrix derivative available from the Swedish company Biora under the trademark EMDOGAIN. Furthermore, a growth factor, nutrient factor, drug, anti-inflammatory agent, anti-bacterial agent, antibiotic, calcium containing compound or combination of these materials may be included in the periodontal structure regeneration composition.

The sponge 15 should be sized to fit within the periodontal pocket and be able to place proper pressure on the bleeding gingiva to stop the bleeding. Therefore, a compressible gauze should be used to allow compaction enabling the gauze to fit the irregular pocket. I prefer to use a modified Nu Gauze surgical sponge that I cut into small strips that are 5 mm to 10 mm wide and 10 cm long. Many surgical sponges including Nu Gauze surgical sponges are made from materials that tear easily with slight pulling force. If this type of gauze is used a piece of torn gauze may be left in the pocket when the sponge is removed. For that reason this type of surgical sponge should not be used. Nevertheless, I have found that such sponges could be modified to contain reinforcing fibers that prevent tearing. The sponge 15 in FIG. 4 is shown to have such reinforcing fibers 19. Further, the gauze can have distinct markings on the ends to determine if the entire gauze strip has been totally removed and that no inadvertent tearing of the gauze that would allow a torn piece to remain in the pocket. The sponge may contain astringents, antibacterial chemicals or antibiotics.

Because the present periodontal structure regeneration compound can be placed in the periodontal pocket to initiate bone growth without surgery, this composition and method for injecting the composition could be used by any dentist.

Figure 6:
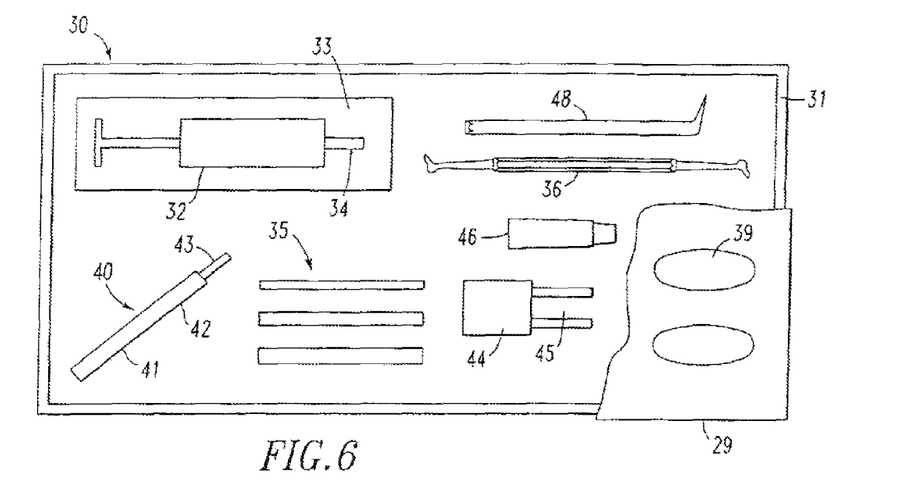
FIG. 6 is a top plan view of a preferred embodiment of a periodontal kit with most of the cover having been cut away.

To make the composition and procedure easier to use I prefer to provide periodontal kits such as are illustrated in FIG. 6. In that figure the relative proportions of the items in the kit are not correct. Smaller items are enlarged and larger items are reduced in a size so that all items could be clearly seen. Each kit 30 is a container 31 with a cover 29 in which there are one or more syringes 32 with 18 gauge needles 34 in a sterile package 33. The syringes are prefilled with from 0.1 ml to 1.0 ml of periodontal structure regeneration compound. If the thickener is of the type that must be mixed with a catalyst to initiate hardening one could use the type of syringe disclosed in U.S. Pat. No. 4,743,229. In this type of syringe the catalyst is in one syringe that is separate from the reminder of the composition that is in a second syringe. The two syringes are connected by a channel that enable the components to be mixed by passage through the channel. The kit also contains a supply of surgical sponges 35 that have been sized into strips to fit within the periodontal pocket. The kit preferably contains three widths of sponges all the same length. The sponges may contain an antibacterial chemical such as peroxide, chlorhexadine, iodine and triiodomethane or other antibacterial chemical. The sponge may also contain a root treatment material, such as a citric acid, fluoride, or EDTA. The sponge may also be impregnated with at least one of epinephrine, alum, aluminum sulfate, aluminum, potassium sulfate, aluminum chloride, oxyguinol sulfate.

Figure 7:
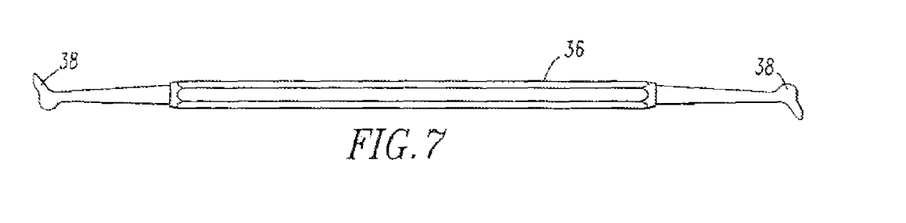
FIG. 7 is a perspective view of a preferred embodiment of a preferred gauze placement tool in the kit of FIG. 6.
Figure 8:
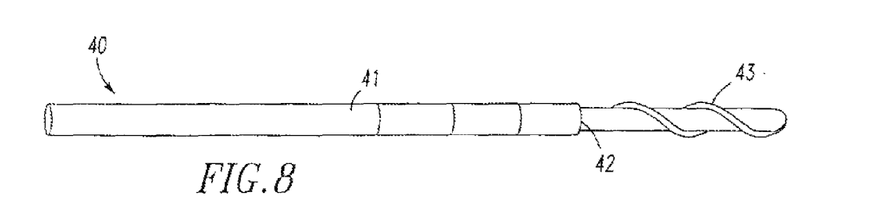
FIG. 8 is a perspective view of a present preferred dental bur in the kit of FIG. 6.

I also prefer to provide a gauze placement instrument 36 shown in FIG. 7. The ends of the gauze placement instrument are shaped to have curved surfaces 38 that conform to the contours of the root of the tooth. Such an instrument can easily be used to place gauze as well as to remove periodontal structure bone regeneration composition after injecting of the composition and to place regeneration composition into wider pockets. The kit may also contain small dental burs 40 shown in FIG. 9 that are used to abrade the inner gingival tissue and root surface. The dental burs of the prior art have a consistent diameter with a rounded or blunt end. Dental bur 40 has a specially shaped tip to allow easy penetration of the pocket, and markings such as lines 42 to indicate depth. The dental bur 40 has a smooth shank 41 and fluted tip 43 similar to 1156, 1157 and 1158 standard dental burs. The shank can be any desired length and diameter. One presently preferred tip comparable to the 1157 model is 0.39 inches (1.00 mm in diameter) and 0.165 inches (4.20 mm) long. The end of the tip 43 is blunt, but tapers to a rounded point. In a preferred embodiment there is 0.39 inches (1.0 mm) from the beginning of the taper to the end of the tip and the tip is rounded. The same specially shaped tip could have a 0.35 inch (0.9 mm) diameter comparable to an 1156, or have a 0.47 inch (1.2 mm) diameter comparable to an 1158. The kit may include more than one dental bur. If more than one size of bur is included, I prefer to color code the shaft of the burs to indicate size. The entire shaft could be colored or colored rings may be applied to the shaft.

I further prefer to include a gauze counter in the kit. This can be a set of depressions 39 in the cover 29 of the kit 30. The depressions could be on an inside surface of the cover or on the outside surface as shown in FIG. 6. Each kit will contain a known number of gauzes. As the gauze is removed from the patient, one gauze is placed in each depression. Then the gauzes are counted to assure that all those that were used have been removed from the patient.

I further prefer to provide a dental bur brush 44 for cleaning the bur during the procedure. This brush preferably has two or three sets of opposed bristles 45 positioned so that the ends of the bristles will engage the dental bur as it is passed through the brush. The kit may also contain a tube of adhesive 46 for sealing the pocket after placement of the periodontal regeneration compound. A probe 48 having marks to measure pocket depth or an end configured to place gauze strips in the pocket may also be included.

The objective of the present method and composition is not merely to achieve bone growth, but rather to regenerate a healthy periodontal structure. This requires not only bone growth but also that the epithelial attachment regenerates. When the epithelial attachment reforms the lost bone beneath the seal will regenerate. Chewing imparts forces to the bone and the bone will grow and strengthen to match the forces.

I have tested various mixtures of hydroxylapatite with collagen in patients suffering periodontal disease. At no time on any patient reported herein have Guided Tissue Regeneration barriers been utilized. The bone regeneration with periodontal structure regeneration procedures alone has achieved similar or superior results as expected with Guided Tissue Regeneration barriers. One patient had generalized 6-10 mm pockets on all 27 teeth. Without incisions, the bur was inserted between the tooth and gingiva completely to the bottom of the pocket. Using the dental drill at slow speed and with appropriate motion, all teeth were subjected to root and gingival abrasion by the bur until all root surfaces were clean and the inner lining of gingiva was abraded. The abraded root material was not rinsed out of the pocket. Gauze strips 5 mm, 7.5 mm and 10 mm wide were placed with the gauze placement instrument into each pocket to create hemostasis and pocket distension. An original source of hydroxylapatite 300-400 micron particles was ground with a mortar and pestle until it was a fine microcrystalline hydroxylapatite powder capable of passing through an 18 ga. needle. A preparation of 1:1 by volume of 1.0 mm sieved collagen particles and microcrystalline hydroxylapatite were mixed with sterile 0.9% saline to make the periodontal structure regeneration material to paste consistency and loaded into a 1 mL. Luer-Lok syringe. The sharp end of a standard 18 ga. 1½ inch Luer-Lok needle was cut off and the end polished to create the blunt needle through which the paste was injected. The gauze was removed after sufficient time elapsed for hemostasis and pocket distension. The periodontal structure regeneration material was then injected into the pocket between the tooth and gingiva until the pocket was filled. Butyl cyanoacrylate adhesive previously loaded into a micropipette was applied about 3 mm on the tooth and 3 mm on the gingiva at their junction to create a protective covering. The butyl cyanoacrylate covered all pockets filled with periodontal structure regeneration material. Water speeds the curing of butyl cyanoacrylate. Water was previously loaded into a micropipette and colored to distinguish the water filled pipette from the butyl cyanoacrylate filled pipette. Small droplets of water were placed on the butyl cyanoacrylate to speed curing. At the two-week post-surgery visit, the pockets were 2-5 mm. At 8 weeks all pockets were 2-3 mm. It was important that the adhesive filled pipette be readily distinguishable from the water filled pipette. Since butyl cyanoacrylate and water look alike one can easily pick up the wrong pipette. Adding a dye to one or the other permits easy distinction. However, since the adhesive remains in place it is better to color the water. One could also use differently shaped or marked pipettes.

A second patient required treatment of both mandibular teeth and maxillary teeth. The mandibular teeth were prepared and treated identically to the maxillary teeth. The only difference was the periodontal structure regeneration material mixture used on the mandibular teeth. A mixture of 2:2:1 of hydroxylapatite:collagen:calcium sulfate by volume was placed into the pockets rather than the 1:1 hydroxylapatite:collagen used on the maxillary teeth. Despite the placement of the gauze, several sites continued to bleed. Upon placement of the periodontal structure regeneration material, bleeding ceased within 10-13 seconds. The surgery lasted 3 hours, no incisions were created, no bleeding occurred. Throughout the post-surgery period the patient did not require pain pills nor did he have swelling. At 8 week post-surgery, most pockets were 2-3 mm with only 2 sites measuring 5 mm. The gingiva remained at the same height with no recession and his oral cosmetics remained unchanged.

A third patient had 27 teeth with 5-9 mm pockets and 11 furcation involvements. All teeth were prepared without incisions utilizing dental bur abrasion, gauze placement, periodontal structure regeneration material placement, and butyl cyanoacrylate covering most treated sites. A mixture of finely ground hydroxylapatite and collagen particles at a 1:1 ratio by volume was injected into the prepared pockets until the pockets were filled. Some areas on the lingual of the mandible, and on the distal of terminal molars were impossible to cover with butyl cyanoacrylate. Those areas remained without a protective adhesive cover and healed as well as other butyl cyanoacrylate covered areas. At 9 weeks post-surgery, we were partially successful with 4 advanced furcation problems that remained with 5-7 mm pockets. All other pockets were 1-3 mm, with the exception of one site at 5 mm. We were successful with 7 furcations that filled in with measurements of 2-3 mm.

A fourth patient had teeth #21-27 remaining. These 7 teeth had extensive horizontal bone loss, but with much of the interproximal gingiva remaining. The 7-8 mm pockets were located interproximal and were soft tissue in nature with little of the pocket resulting from osseous defects. The 7-8 mm pockets occurred within 4 months. A particularly aggressive bacteria probably was the etiology of the rapid destruction of the periodontal structure called the epithelial attachment that attaches the gingiva to the tooth. To help destroy the bacteria, prior to placement, the gauze was soaked with an oxygenating solution. The solution releases oxygen. The oxygen causes both hemostasis and is bacteriocidal. All teeth were prepared without incisions utilizing dental bur abrasion, gauze placement, periodontal structure regeneration material placement, and butyl cyanoacrylate covering all treated sites. The periodontal structure regeneration material was 1:2 hydroxylapatite:collagen by volume. By 4 weeks post-surgery, his pockets were all 2-3 mm indicating that the periodontal structure regenerated.

A fifth patient had 27 teeth of which 25 were treated. Mobility on 17 of the teeth was from a minor+mobility to 1 on a standard dental scale. Pockets ranged from 6-8 mm with 7 furcation problems. All teeth were prepared without incisions utilizing dental bur abrasion, gauze placement, periodontal structure regeneration material placement, and butyl cyanoacrylate covering all treated sites. Several persistent bleeding sites that would not stabilize with pressure, nor with injection of a xylocaine with epinephrine, immediately ceased bleeding upon the placement of butyl cyanoacrylate over the sites. Periodontal structure regeneration material was prepared with a ratio of 3:2:1 hydroxylapatite:collagen:calcium sulfate. Included is a tally of the number of pocket readings pre-surgery and 12 week post-surgery on #4-13, 20-27. A total of 108 readings for the 18 teeth.

| Pre-surgery | Post-surgery |
|---|---|
| 1 mm 0 | 1 mm 66 |
| 2 mm 13 | 2 mm 28 |
| 3 mm 36 | 3 mm 14 |
| 4 mm 26 | 4 mm 0 |
| 5 mm 14 | 5 mm 0 |
| 6 mm 8 | 6 mm 0 |
| 7 mm 10 | 7 mm 0 |
| 8 mm 1 | 8 mm 0 |

The high number of post-surgery readings of 1 mm and 2 mm is extraordinary. Readings of 1 mm are rarely seen in healthy patients, and few 2 mm are seen in healthy patients. Mobility on all teeth was zero. One furcation completely healed, while 6 furcations reduced from 5-8 mm to 2-5 mm but were still Class I and Class II.

Only 6 teeth were treated on a fifth patient, but the damage was severe. Teeth #9, 22-25, 27 are anterior teeth where cosmetics are paramount. Standard periodontal surgical treatment of this anterior area utilizing incisions removes large amounts of gingiva. Gingival recession with root exposure is a major problem for the periodontist, and of great cosmetic concern for the patient. Tooth #9 had an expensive ceramic facing adding an additional complication to treatment. Any gingival recession would expose the facing margin and defeat the cosmetic dentistry. All teeth were prepared without incisions utilizing dental bur abrasion, gauze placement, periodontal structure regeneration material placement, and butyl cyanoacrylate covering all treated sites. The periodontal structure regeneration material was 3:2:1 hydroxylapatite:collagen:calcium sulfate. After 9 weeks, the pockets were all 1-2 mm with one 3 mm site. The 10 mm site was now 2 mm. No gingival recession occurred. There were no cosmetic complications and the ceramic facing was not exposed.

A sixth patient had 6 to 10 mm pockets. Fourteen days after treatment the pockets were about 4 mm deep. This decreased depth cannot be from bone regeneration in such a short time. Bone really requires many weeks and months to fully form. Bone precursor tissue grew and filled in the space, but that still does not account for the rapid decrease in pocket depth. The soft tissue structures of gingiva, underlying fibrous connective tissue, periodontal ligament, and epithelial attachment probably were forming concurrently thus decreasing the depth. Much of the greatly enhanced speed of healing comes from the properties attributed to free collagen. Before healing can begin, hemostasis must occur. Medical literature states that collagen applied to a wound at the time of hemostasis acts as an assistive mechanism to augment clotting. Collagen actually increases platelet adherence to the endothelial vessel walls, thus sealing them off. Fibroblasts combine and build amino acids into a sugar protein structure to form collagen at the wound site. This advances the wound environment by five or six days. Collagen also attracts additional monocytes to the wound, thus increasing the amount of debris removed, which leads to speedier wound healing. During angiogenesis, collagen assists with epithelialization of the endothelial lining of the blood vessel wall. By developing this system a healthy wound will develop and healing occurs.

The particular compositions used to treat these six patients contained collagen material that I obtained from BioCore, Inc. I also treated patients using a composition that contained hydroxylapatite and collagen obtained from other sources. One such collagen was Avitene collagen sold in sheets 35 mm×35 mm×1 mm. The sheets crumbled under very light pressure. I mixed the Avitene collagen with the hydroxylapatite powder and saline and applied them to the patient. The Avitene collagen did not affect the rate of healing. I had obtained similar results using hydroxylapatite without collagen.

A BioCore brochure titled "Kollagen Technology" pamphlet published in 1999 says, "Many products on the market claim to be collagen. And while they may start with Type I collagen, their processing alters the molecular structure to the point where, under a microscope, it is no longer identifiable as true collagen. When a product lists "denatured" or "hydrolyzed" collagen as one of its ingredients, it means that structure has been changed to the point where it fails to meet the scientifically accepted definition of collagen. These products exhibit no biological response that aids in wound healing. The term "biological response" is an important distinction. Many collagen products exhibit the properties of a physical dression . . . . But they don't evoke a biological response because the collagen is not in the proper form for the body to recognize it as native. Kollagen (which is the tradename for Biocore collagen) products maintain the chemistry and structure of collagen. They contain complete molecules and fibrils. They form aggregates with a triple-helix rope-like structure. And most importantly, they elicit a biological response necessary to promote wound healing."

I also treated a patient with a mixture of hydroxylapatite and Collastat collagen. The Collastat collagen is a fibrous material similar to a tuft of cotton. I was unable to cut the Collastat collagen into pieces small enough to pass through an 18 gauge needle. Therefore, I applied the collagen and hydroxylapatite using spatulas to periodontal pockets. The results using the Collastat collagen were no different than results achieved without collagen.

I attempted to determine why the BioCore collagen speeded healing and bone regeneration while the Avatene collagen and the Collastat collagen did not BioCore would not reveal the composition or method of manufacture of BioCore collagen. However, I did learn that unlike other collagens available in the market, BioCore collagen is not treated with glutaraldehyde. Glutaraldehyde acts as a cross-linker of collagen molecules. BioCore stated that their collagen is the only collagen that is not hydrolyzed or further cross-linked, worldwide. Furthermore, 90% of the fibrillar collagen is still intact after their mild proprietary processing methods.

I believe that the Avitene collagen and the Collastat collagen are cross-linked structures. However, they did not speed healing like the BioCore collagen. Apparently, the cross-linking prevents the Avitene and Collastat collagen from acting like the free collagen. Jeffries in U.S. Pat. Nos. 4,394,370 and 4,472,840 describes collagen treated with glutaraldehyde as forming a sponge when dried. Chen et al. U.S. Pat. No. 5,707,962 discloses methods of using this collagen sponge described by Jeffries. Consequently, the composition disclosed by Jeffries and Chen, in which collagen has been cross-linked, would not be expected to speed healing, like the compositions disclosed here containing free collagen.

From the foregoing examples it can be seen that the periodontal structure regeneration material can vary in composition but contains at least one bone growth material and free collagen. Suitable materials include a mixture of a fine microcrystalline hydroxylapatite powder, some 50-400 micron hydroxylapatite particles, free collagen particles, and calcium sulfate in varying percentages. This collagen has been used in small particles less than 1 mm, and collagen has been used in a gel form in the mixtures. The hydroxylapatite used in the mixture was 100% microcrystalline, or a mixture of mostly microcrystalline material with some larger particles varying from approximately 50 microns to about 400 microns in diameter. Calcium sulfate has been used in varying percentages. I have also used finely ground bone with collagen in varying percentages. Other periodontal regeneration materials contained bovine bone used as a finely ground powder and free collagen in varying percentages. Various ceramic glass bone growth materials have been used with free collagen in varying percentages. All of these variations have created periodontal structure regeneration.

Although I have disclosed several formulations in which BioCore collagen was used, the invention is not limited to compositions containing collagen provided by BioCore. Inc. Any collagen material can be used that contains collagen particles that are not cross-linked and that speeds healing. The composition may also include other materials in addition to those disclosed here, provided those other materials do not cause significant amounts of free collagen to cross-link and those other materials are suitable for use in a periodontal pocket.

While I have described certain present preferred embodiments of my periodontal structure regeneration composition as well as methods and tools for using that composition, it should be distinctly understood that the invention is not limited thereto, but may be variously embodied within the scope of the following claims.

I claim:

1. A bone growth and adjacent tissue regeneration composition for treatment of bone loss comprising a mixture of particles of a bone growth material, free collagen, a thickener and a fluid wherein the thickener is a physiological compatible compound that slowly forms an insoluble salt with at least one component in the mixture.

2. The composition of claim 1 wherein the thickener is a physiologically compatible compound which is liquid above a physiological temperature.

3. The composition of claim 2 wherein the compound is an oligosaccharide.

4. The composition of claim 3 wherein the oligosaccharide is a polyethylene glycol.

5. The composition of claim 1 wherein the thickener is a material that is activated by at least one of air, heat, light and a catalyst.

6. The composition of claim 1 wherein the thickener is a material that absorbs water.

7. The composition of claim 1 further comprising an adhesive placed over a portion of the mixture, the adhesive being selected from the group comprising water curable adhesives, visible light curable adhesives, auto curing adhesives, heat curable adhesives, reactive-component cure adhesives, surface activated adhesives, and curable adhesives that cure when exposed to ultraviolet radiation.

8. The composition of claim 1 further comprising wherein the mixture is subjected to infusion of energy from at least one energy source sufficient to dissociate the collagen fiber without denaturing proteins in the collagen fibers and to allow at least some of the particles of bone growth material to be captured between adjacent collagen fibers after the infusion of energy has ceased.

9. The composition of claim 8 in which the energy source is selected from the group consisting of a water bath, an oil bath, a microwave source, a radiant heat source, and a sonicator.

10. The composition of claim 7 further comprising wherein an infusion of energy is provided by heating the composition in one of an oven, a water bath, and an oil bath.

11. The composition of claim 1 further comprising wherein the composition is heated to a temperature at least 110° F. for a time period sufficient to cause the collagen fiber in the composition to melt but not to degrade.

12. The composition of claim 11 wherein the heat is provided by a water bath between 110° F. and 180° F.

13. The composition of claim 11 wherein the heat is provided by a water bath between 120° F. and 160° F. for less than 20 minutes.

14. The composition of claim 1 further comprising at least one material selected from the group consisting of growth factors, nutrient factors, drugs, calcium containing compounds, anti-inflammatory agents, anti-microbial agents, root treatment materials, bone morphogenic proteins, dental matrix derivatives, and combinations thereof.

15. The composition of claim 1 further comprising wherein the bone growth material is a material selected from the group consisting of human bone particles, hydroxyapatite, animal bone particles, ground coral, calcium sulfate, calcium carbonate, substituted and unsubstituted calcium phosphate cements, bioactive glasses, polymers that promote bone growth and combinations thereof.

16. The composition of claim 1 further comprising at least one matrix forming material selected from the group consisting of cross-linked collagen, water soluble polymers, gelling polymers, hydrocolloids, hydrogels, polyethyleneglycols, natural polymers, chemically modified natural polymers, synthetic polymers and copolymers, colloids, thermosetting polymers and thermoplastic polymers.

17. The composition of claim 16 wherein at least one of the matrix-forming materials gets more viscous at or below 98.6° F.

18. The composition of claim 16 wherein at least one of the matrix-forming materials melts at or above 98.6° F.

19. The composition of claim 1 further comprising wherein the composition, after formulation, is stored in one selected from the group consisting of a refrigerator at a temperature above 32° F. and a freezer at a temperature below 32° F.

20. The composition of claim 1 wherein the fluid is a biocompatible fluid selected from the group consisting of normal saline, water, and inorganic salt solutions.

21. The composition of claim 1 wherein up to 10% of the total fluid volume is comprised of a biocompatible and water-miscible organic solvent.

* * * * *

UNITED STATES PATENT AND TRADEMARK OFFICE
CERTIFICATE OF CORRECTION

PATENT NO. : 10,004,806 B2  
APPLICATION NO. : 13/655969  
DATED : June 26, 2018  
INVENTOR(S) : Dennis W. Szymaitis Page 1 of 1

It is certified that error appears in the above-identified patent and that said Letters Patent is hereby corrected as shown below:

On the Title Page

The last sentence in the ABSTRACT, The composition is available in pre-filled syringes offered in a kit that may also contain strips of surgical sponge or gauze that are sized to fit within a periodontal pocket, a time of adhesive, a dental bur, a probe, a gauze placement tool, gauze counter and a brush for cleaning the dental bur., should be corrected to, The composition is available in pre-filled syringes offered in a kit that may also contain strips of surgical sponge or gauze that are sized to fit within a periodontal pocket, a tube of adhesive, a dental bur, a probe, a gauze placement tool, gauze counter and a brush for cleaning the dental bur.

In the Specification

Column 2, Line 13 discomfort pain, swelling, gingival recession, sensitive should read discomfort, pain, swelling, gingival recession, sensitive Column 12, Line 36 collagen and the Collastat collagen did not BioCore would should read collagen and the Collastat collagen did not. BioCore would Signed and Sealed this  
Twenty-eighth Day of August, 2018

Andrei Iancu  
*Director of the United States Patent and Trademark Office*